128/660

United States Patent [19]

Putzke

[11] Patent Number: 4,567,895

[45] Date of Patent: Feb. 4, 1986

[54] FULLY WETTED MECHANICAL ULTRASOUND SCANHEAD

[75] Inventor: Dwayne H. Putzke, Issaquah, Wash.

[73] Assignee: Advanced Technology Laboratories, Inc., Bothell, Wash.

[21] Appl. No.: 595,888

[22] Filed: Apr. 2, 1984

[51] Int. Cl.[4] .......... A61B 10/00

[52] U.S. Cl. .......... 128/660; 73/639

[58] Field of Search .......... 128/660–661, 128/663; 73/610–620, 621, 639

[56] References Cited

U.S. PATENT DOCUMENTS

| | | | |
|---|---|---|---|
| 3,964,296 | 6/1976 | Matzuk | 73/625 X |
| 4,034,744 | 7/1977 | Goldberg | 128/660 |
| 4,047,520 | 9/1977 | Soldner et al. | 128/660 |
| 4,149,419 | 4/1979 | Connell, Jr. et al. | 128/660 X |
| 4,231,373 | 11/1980 | Waxman et al. | 128/660 |
| 4,269,066 | 5/1981 | Fischer | 128/660 X |
| 4,418,698 | 6/1983 | Dory | 128/660 |

*Primary Examiner*—Kyle L. Howell
*Assistant Examiner*—Francis J. Jaworski
*Attorney, Agent, or Firm*—Lawrence S. Levinson; Sanford J. Asman

[57] ABSTRACT

A fully wetted ultrasound scanhead for medical applications is described in which the motor and the rotor are enclosed within a sealed housing filled with ultrasound coupling fluid. The invention includes a drive belt to drive the rotor from the motor, rather than a precision drive means. Speed adjustment means, including an encoder disk mounted on the rotor, provide feedback for an electronic speed controller. Accordingly, the speed of the motor can be adjusted as a direct consequence of the actual speed of the rotor.

8 Claims, 5 Drawing Figures

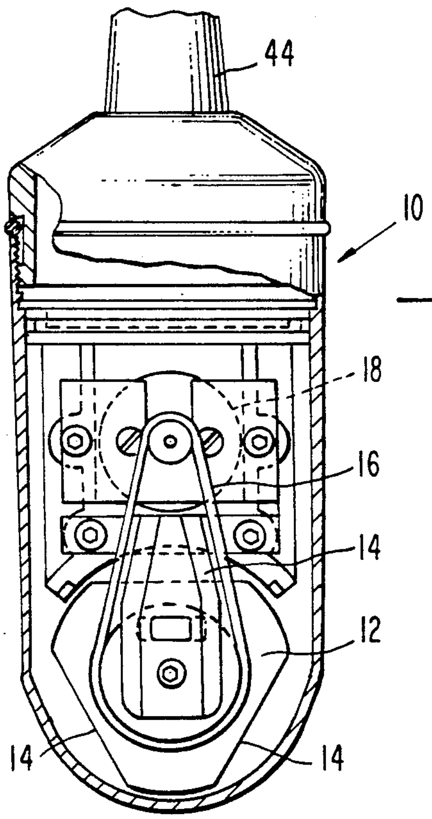
FIG. 1.
FIG. 5
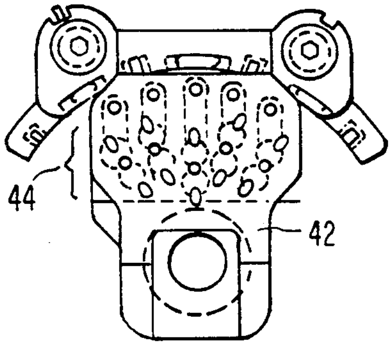
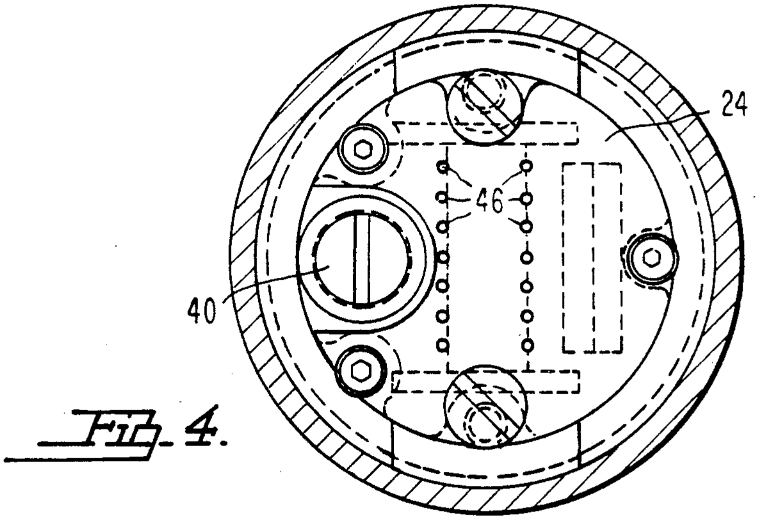
FIG. 4.

FULLY WETTED MECHANICAL ULTRASOUND SCANHEAD

BACKGROUND OF THE INVENTION

The present invention relates to mechanical scanheads. In particular, it relates to a mechanical scanhead of the type used in medical electronic diagnostic ultrasound equipment.

Ultrasound is a non-invasive technique for generating image scans of interior body organs. As is well known in the art, there are a variety of types of ultrasound transducers. These include elongated transducers, such as phased array transducers and linear array transducers which are fully electronic in beam forming and directing, and various types of spherical transducers and annular arrays, which are typically scanned mechanically.

Mechanical scanheads typically utilize two techniques for generating sector scans. The first technique, which requires a plurality of transducers, is the rotating scanhead unit, in which the various transducers are rotated through 360 degrees and are turned on in succession over a sector which corresponds to the sector being scanned. The second type of mechanical scanhead is an oscillating scanhead, sometimes called a "wobbler". In either type of mechanical scanhead, drive means, such as a motor, must be connected to the transducer in order to impart mechanical movement to the rotor. In typical mechanical scanheads, of the type heretofore used, the motor drive means is in a dry ambient whereas the ultrasound transducer is typically immersed in an acoustic coupling medium such as mineral oil. A problem which has heretofore existed with mechanical scanheads, especially those which require a plurality of transducers, is that they are very expensive to manufacture due to the critical alignment of the various parts from which they are made. In addition, there has always been a problem with the seals between the dry portion of the scanhead, in which the motor is located, and the wet portion of the scanhead in which the transducer is located. Heretofore, there has also been a problem with determining the exact position of the ultrasound transducer to a high degree of accuracy when the encoder was mounted on the motor shaft. This has required that very accurate, and expensive, precision gearing be used to connect the scanhead to the motor. As a result of the use of both a wetted area and a dry area and the use of precision gears, mechanical scanheads have typically been rather large when compared to phased array transducers. The excessive size of mechanical scanheads has made them somewhat unwieldy to use in some applications. Consequently, a less expensive, more reliable, and smaller mechanical scanhead would be highly desirable.

SUMMARY OF THE INVENTION

The present invention is an improved mechanical ultrasound scanhead. The scanhead includes a sealed housing with a rotor mounted in it. The rotor has at least one ultrasound transducer mounted on it, and the housing contains an ultrasound coupling fluid. The improvement in the present invention is that the motor is mounted in the sealed housing, and the motor is coupled to the rotor by means of a drive belt rather than through precision gearing. An encoder disk, mounter on the rotor, is used in conjunction with feedback electronics to control the speed of the rotor, whereby said motor is fully wetted by the ultrasound coupling fluid.

BRIEF DESCRIPTION OF THE DRAWINGS

FIG. 1 is a top cross-sectional view of the ultrasound scanhead of the present invention;

FIG. 4 is a rear cross-sectional view of the present invention taken along the lines 4—4 of FIG. 2; and FIG. 5 is a plan view of the decoder apparatus used in the present invention.

DETAILED DESCRIPTION OF THE INVENTION

Figure 2:
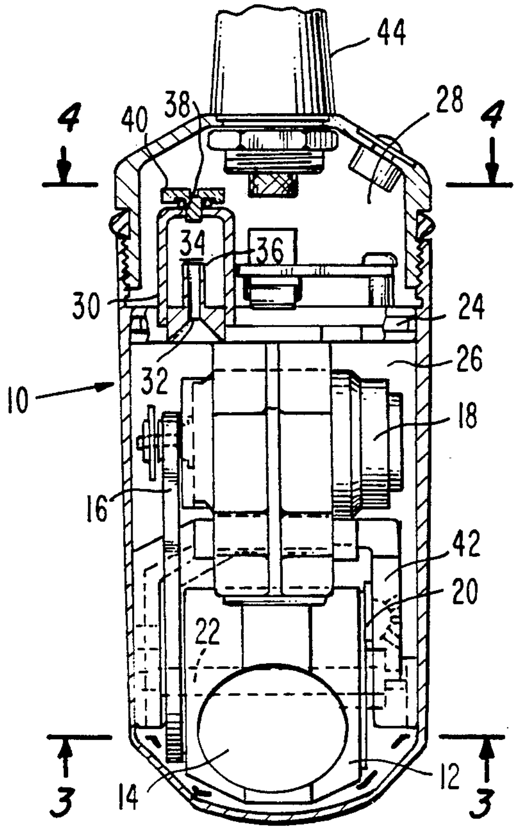
FIG. 2 is a side cross-sectional view of the scanhead of the present invention.
Figure 3:
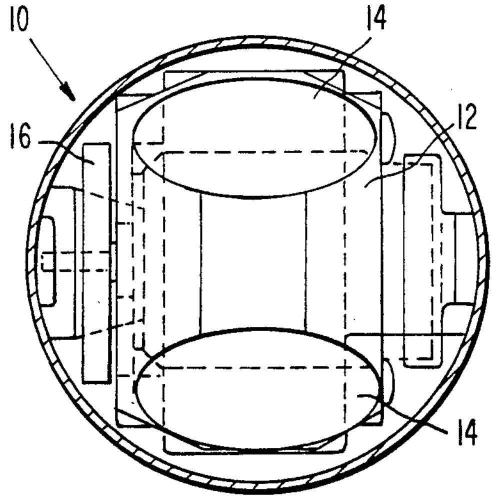
FIG. 3 is a front cross-sectional view of the present invention taken along the lines 3—3 of FIG. 2.

Referring now to FIGS. 1 and 2, cross-sectional views of the fully wetted mechanical scanhead 10 made in accordance with the present invention are shown. The scanhead 10 comprises a rotor 12 which houses three transducers 14. These transducers 14 are spherical transducers which may have the same frequency or which may have multiple frequencies, as is well known in the art.

The transducers 14 are mounted on the rotor 12 which is connected via a drive belt 16 to an electric motor 18. Both the motor 18 and the rotor 12 are mounted in close proximity to one another in a sealed housing 26 within the scanhead 10. The use of the sealed housing 26, filled with an ultrasound coupling fluid, i.e., "a fully wetted region", represents a departure from the typical rotating scanhead which would separate the rotor from the motor and would place the rotor in a wet environment and the motor in a dry environment. Also, the use of the drive belt 16, a non-precision item, means that the scanhead 10 is significantly less expensive to manufacture than a scanhead having a conventional design which would require a precision gear and seal, of the type heretofore used.

The reason that the scanhead 10 is able to use a non-precision arrangement to drive the rotor 12 from the motor 18 is that the scanhead 10 does not use an encoding device which mounted on the motor 18. In the present invention, however, an encoder disk 20 is mounted on the shaft of the rotor 12. Accordingly, feedback means which include LED's and the encoder disk 20, can accurately keep track of the precise position of the rotor 12. In the scanheads of the prior art, even those using precision gearing, the precise position of the rotor could only be determined inferentially. In the present invention, however, even though significantly less expensive means are used to move the rotor 12, the exact position of the rotor 12 can be determined. The specific encoder arrangment which is used in the present invention is comprised of an encoder disk 20 having a series of reflective and non-reflective lines thereon. The lines are scanned by phototransmissive elements, LEDs in the preferred embodiment, and reflections are picked up by photoreceptive elements, phototransistors in the preferred embodiment. A unique feature of the present invention that the photoelements are mounted within the sealed housing containing the ultrasound coupling fluid. Accordingly, the optical characteristics of the ultrasound coupling fluid must be accounted for by the encoder optics. Accordingly, the photoelements are mounted in close proximity to the encoder disk, and, in the preferred embodiment of the invention, no lenses are used on the photoelements.

Other features of the present invention which help to minimize manufacturing costs without sacrifice to reliability or performance, include the fully molded mounting base into which the rotor is fitted.

The particular motor 16 which is used in the preferred embodiment of the invention is a shaft mounted motor in which the casing rotates.

With continued reference to FIG. 2, the scanhead 10 further comprises a sealing bulkhead 24 which separates the sealed housing 26 from the dry portions in the cavity 28. Mounted on the bulkhead 24 is a bubble trap 30 which permits gas bubbles to rise through a funnel-like aperature 32 into a cavity 34. When the cavity 34 is filled with fluid to a point higher than the top 36 of the funnel-like aperature 32, bubbles trapped in the bubble trap 30 cannot escape. Periodically, gas is removed from the bubble trap 30 by injecting additional fluid through an opening 38 by removing a screw cap 40 (See FIG. 4).

As stated above, the encoding apparatus is comprised of a unit 42 (See FIG. 5) on which the phototransistors and LEDs are mounted in pairs at locations generally designated 44. The specific operation of the encoding apparatus is not relevant to the present invention other than to say that reflections of light from the LEDs (not shown) off the encoding disk 20 provide a speed feedback mechanism for adjusting the speed of the motor 18, thereby adjusting the speed of the rotor 12, through external electronics (not shown). The external electronics use signals on a cable 44 which passes through the bulkhead 24 through a series of holes 46 form therein.

I claim:

1. An improved mechanical ultrasound scanhead of the type comprising a sealed housing, a rotor mounted in said sealed housing, said rotor having a plurality of ultrasound transducers mounted thereon, and said sealed housing being filled with an ultrasound coupling fluid, wherein the improvement comprises:

(a) a motor mounted in said sealed housing, said motor being fully immersed in said ultrasound coupling fluid and said motor being coupled to said rotor by means of a drive belt; and (b) means, on said rotor, for controlling the speed of said rotor, whereby said motor, said rotor, said drive belt, and said means for controlling the speed of said rotor are all fully wetted by said ultrasound coupling fluid.

2. The improved mechanical ultrasound scanhead of claim 1 wherein said motor is a shaft mounted DC motor.

3. The improved mechanical ultrasound scanhead of claim 2 wherein said means, on said rotor, for controlling the speed of said motor comprises an encoder disk having reflective and non-reflective markings thereon.

4. The improved mechanical ultrasound scanhead of claim 3 further comprising means for sensing the presence of said reflective and non-reflective markings on said encoder disk.

5. The improved mechanical ultrasound scanhead of claim 4 wherein said means for sensing the presence of said reflective and non-reflective markings on said encoder disk comprises a series of phototransmissive and photoreceptive elements.

6. The improved mechanical ultrasound scanhead of claim 5 wherein said phototransmissive and photoreceptive elements are comprised of LEDs and phototransistors, repectively.

7. The improved mechanical ultrasound scanhead of claim 6 wherein said LEDs and phototransistors are mounted within said sealed housing.

8. The improved mechanical ultrasound scanhead of claim 7 wherein said LEDs and phototransistors are adjacent to one another and to said encoder disk, whereby the optical properties of said ultrasound coupling fluid are used, in lieu of lenses, between said LEDs and phototransistors, and said encoder disk.

* * * * *